United States Patent
Joo et al.

(10) Patent No.: US 6,881,865 B2
(45) Date of Patent: Apr. 19, 2005

(54) METHOD FOR PREPARING CYCLOHEXYL PHENYL KETONE FROM 1,3-BUTADIENE AND ACRYLIC ACID

(75) Inventors: Young J. Joo, Daejeon (KR); Jin Eok Kim, Daejeon (KR); Jeong Im Won, Daejeon (KR); Tae Yi Kang, Daejeon (KR)

(73) Assignee: Korea Kumho Petrochemical Co., Ltd. (KR)

( * ) Notice: Subject to any disclaimer, the term of this patent is extended or adjusted under 35 U.S.C. 154(b) by 0 days.

(21) Appl. No.: 10/628,800

(22) Filed: Jul. 28, 2003

(65) Prior Publication Data

US 2004/0073068 A1 Apr. 15, 2004

(30) Foreign Application Priority Data

Sep. 27, 2002 (KR) .............................. 10-2002-0058627

(51) Int. Cl.$^7$ ............................................... C07C 45/48
(52) U.S. Cl. ...................... 568/314; 568/316; 568/317; 568/318; 568/321; 568/329
(58) Field of Search ................................ 568/314, 316, 568/317, 318, 321, 329

(56) References Cited

U.S. PATENT DOCUMENTS

| 3,660,491 A | 5/1972 | Thigpen et al. ............. 260/592 |
| 4,950,763 A | 8/1990 | Schommer et al. ......... 546/314 |

FOREIGN PATENT DOCUMENTS

| GB | 1030003 | 5/1966 |
| GB | 1063268 | 3/1967 |

OTHER PUBLICATIONS

Cope et al., "N,N–Dimethylcyclohexylmethylamine", Organic Syntheses, vol. IV, pp. 339–342.

*Primary Examiner*—Johann Richter
*Assistant Examiner*—Sikarl A. Witherspoon
(74) *Attorney, Agent, or Firm*—Dilworth & Barrese LLP

(57) ABSTRACT

Disclosed is a synthesis method of cyclohexyl phenyl ketone with a high selectivity and a high yield from 1,3-butadiene and acrylic acid in the presence or absence of benzene or a non-aromatic organic solvent in the same reaction without a step of separating or purifying intermediates, the synthesis method including sequentially carrying out a [2+4] Diels-Alder reaction, a hydrogenation reaction, a chlorination reaction and a Friedel-Crafts reaction in the presence/absence of benzene or a non-aromatic organic solvent without separation of intermediates.

11 Claims, No Drawings

METHOD FOR PREPARING CYCLOHEXYL PHENYL KETONE FROM 1,3-BUTADIENE AND ACRYLIC ACID

CROSS REFERENCE TO RELATED APPLICATIONS

This application claims priority to Korean Patent Application 2002-0058627 filed on Sep. 27, 2002 under 35 U.S.C. §119.

BACKGROUND OF THE INVENTION

1. The Field of the Invention

The present invention relates to a method for preparing a cyclohexyl phenyl ketone from a 1,3 butadiene and acrylic acid without a purification or separation step and, more particularly, to a synthesis method of cyclohexyl phenyl ketone that includes carrying out a [2+4] Diels-Alder reaction of 1,3-butadiene and acrylic acid in the presence or absence of benzene or a non-aromatic organic solvent to yield 3-cyclohexene-1-carboxylic acid, a hydrogenation reaction to yield cyclohexanecarboxylic acid, a chlorination reaction to prepare a cyclohexanecarbonyl chloride; and a Friedel-Crafts reaction in the same reactor without purifying or separating the cyclohexanecarboxylic acid to prepare a cyclohexyl phenyl ketone with a high yield.

2. Related Prior Art

In general, cyclohexyl phenyl ketones are used as an intermediate of 1-hydroxy cyclohexyl phenyl ketone that is used as a photoinitiator in a photopolymerization reaction of unsaturated compounds and a photochemical cross linking reaction of polyolefins.

The potoinitiator is a curing agent that temporarily converts a liquid material to a solid resin using an ultraviolet radiation, and widely applied for a UV coating material, a UV ink, etc., in the manufacture of special high gloss furniture, wrapping paper printing, or high gloss plastic floor material.

The most generally used method for preparing a cyclohexyl phenyl ketone involves hydrogenation of benzoic acid under the condition of high temperature and high pressure, purification for removal of by-products to yield a cyclohexanecarboxylic acid, conversion of the purified cyclohexanecarboxylic acid to a cyclohexanecarbonyl chloride (Ref. Organic Synthesis, col. Vol. IV, 339–342), and Friedel-Crafts reaction with benzene in the presence of anhydrous aluminum trichloride.

This method, which produces a cyclohexyl phenyl ketone with a high yield, requires a condition of high temperature and high pressure for the hydrogenation reaction of benzoic acid, with the difficulty in regard to production facilities, and the purification step for removing by-products of the hydrogenation reaction.

Another known synthesis method of cyclohexyl phenyl ketones involves reacting cyclohexanecarboxylic acid with benzoic acid in the presence of a manganate catalyst such as manganese carbonate (MnCO₃), as disclosed in UK Patent Nos. 1,030,003 and 1,063,268. This method has the difficulty in regard to production facilities due to high reaction temperature(280–450° C.).

U.S. Pat. No. 4,950,763 discloses a method of preparing a cyclohexyl phenyl ketone from cyclohexanecarboxylic acid and benzoic acid in the presence of a titanium oxide catalyst including alkali oxides by a gas phase reaction, which method is inferior in selectivity. U.S. Pat. No. 3,660,491 also discloses a method of preparing a cyclohexyl phenyl ketone from cyclohexanecarboxylic acid and benzoic acid. This method is carried out in the presence of a cobalt catalyst at a low temperature of below 200° C. but with a low conversion rate.

In addition, UK Patent No. 1,066,542 discloses a synthesis method of a cyclohexyl phenyl ketone from cyclohexanecarboxylic acid and benzene in the presence of polyphosphate, which method has a very low product yield.

SUMMARY OF THE INVENTION

In an attempt to develop a synthesis method of cyclohexyl phenyl ketone with a high selectivity and a high yield, the inventors of the present invention have contrived a synthesis method of cyclohexyl phenyl ketone very useful for the industrial use that includes carrying out a [2+4] Diels-Alder reaction of 1,3-butadiene and acrylic acid as starting materials without the formation of by-products and sequentially carrying out hydrogenation, chlorination and Friedel-Crafts reactions in the same reactor without a step of separating or purifying intermediates.

It is therefore an object of the present invention to provide a synthesis method of cyclohexyl phenyl ketone with a high yield and a high selectivity that prevents the formation of by-products without a step of separating or purifying intermediate or being affected by any catalyst used.

To achieve the above object of the present invention, there is provided a method for preparing a cyclohexyl phenyl ketone from a 1,3-butadiene and an acrylic acid, the method including: (a) carrying out a [2+4] Diels-Alder reaction of the 1,3-butadiene and the acrylic acid in the presence or absence of a solvent to prepare a 3-cyclohexene-1-carboxylic acid; (b) carrying out a hydrogenation reaction of the 3-cyclohexene-1-carboxylic acid to prepare a cyclohexanecarboxylic acid; (c) carrying out a chlorination reaction in the solution of the cyclohexanecarboxylic acid without separation or purification of the cyclohexanecarboxylic acid to prepare a cyclohexanecarbonyl chloride; and (d) continuously carrying out a Friedel-Crafts reaction of the cyclohexanecarbonyl chloride in the same reactor without separation or purification of an intermediate to prepare a cyclohexyl phenyl ketone.

The present invention is directed to a method for preparing a cyclohexyl phenyl ketone from a 1,3-butadiene and an acrylic acid in the same reactor without a separation or purification step.

The exemplary mechanism of the synthesis method of the present invention can be expressed as follows:

Reaction 1

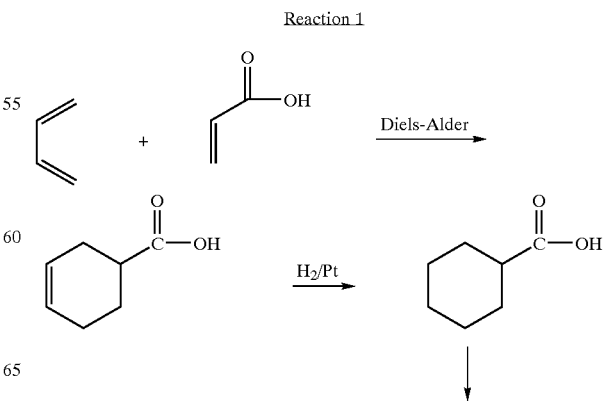

-continued

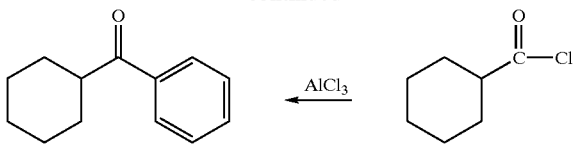

In the synthesis mechanism of cyclohexyl phenyl ketone, a [2+4] Diels-Alder reaction using a 1,3-butadiene and an acrylic acid is carried out in the presence or absence of a solvent under the condition that no side reaction occurs, to prepare a 3-cyclohexene-1-carboxylic acid. The 3-cyclohexene-1-carboxylic acid is subjected to a hydrogenation reaction to yield a cyclohexanecarboxylic acid with a high conversion rate.

Then, thionyl chloride or the like is added to the solution of the cyclohexanecarboxylic acid at a relatively low temperature without separating the cyclohexanecarboxylic acid from the solution, to prepare a cyclohexanecarbonyl chloride. Subsequently, anhydrous aluminum trichloride is added directly to the solution of the cyclohexanecarbonyl chloride to prepare a cyclohexyl phenyl ketone by a Friedel-Crafts reaction.

Namely, the present invention method is a synthesis method that involves separation of the final product, cyclohexyl phenyl ketone solely without separating intermediates in the intermediate steps.

This method requires no separation or purification step, thus reducing the complexity of the process, and prepares cyclohexyl phenyl ketone with a high yield.

In the first reaction i.e., the [2+4] Diels-Alder reaction of 1,3-butadiene and acrylic acid, a solvent can be used or not. If used, the solvent can be benzene selected in consideration of the synthesis of the final product, or a non-aromatic organic solvent not affecting the Friedel-Crafts reaction, thereby preventing any side reaction in the final step. This solvent system does not cause a problem such as the formation of by-products in the hydrogenation, chlorination and Friedel-Crafts reactions.

Specific examples of the non-aromatic organic solvent includes aliphatic hydrocarbons such as cyclohexane, hexane, heptane and octane; tetrahydrofuran (THF); dioxane; ethers; or a mixture thereof.

Preferably, the reactions are carried out under the condition that a side reaction is prevented by adding a polymerization inhibitor of 1,3-butanene and acrylic acid and that the reaction temperature and the ratio of the reactants are controlled to guarantee an acrylic acid conversion rate of more than 99%. More specifically, the reaction temperature is in the range of 80 to 200° C., preferably 120 to 150° C.

Here, the polymerization inhibitor can be 4-t-butylcatechol.

The molar ratio of 1,3-butadiene to the acrylic acid is used 1:1.1 to 1:2, preferably 1:1.2 to 1:1.5.

After the completion of the reaction, a predetermined amount of a heterogeneous hydrogenation catalyst is added to the reactant solution and a hydrogenation reaction is carried out to generate a cyclohexanecarboxylic acid under the condition that the temperature is from 80 to 120° C. and the hydrogen pressure is from 80 to 120 psi. Specific examples of the heterogeneous hydrogenation catalyst as used herein may include platinum(Pt/C) and palladium(Pd/C).

Subsequently, a chlorination reactant such as thionyl chloride or phosphorous trichloride is added to the solution of the cyclohexanecarboxylic acid prepared from the hydrogenation reaction at a molar ratio of 1 to 3, preferably 1 to 2 with respect to the cyclohexanecarboxylic acid for chlorination reaction, thereby quantitatively prepare a cyclohexanecarbonyl chloride.

To the solution, anhydrous aluminum trichloride is added at a molar ratio of 1 to 3 with respect to the cyclohexanecarbonyl chloride, without removing the reactant solution of the chlorination product. If the solvent used herein is not benzene, benzene is added at a molar ratio of 1 to 3 with respect to the cyclohexanecarbonyl chloride to prepare the final product, cyclohexyl phenyl ketone by the Friedel-Crafts reaction.

The process of the present invention is a commercially very useful method of preparing a cyclohexyl phenyl ketone with high selectivity and high yield by using a synthesis mechanism not requiring separation or purification of the intermediates in the intermediate steps.

The [2+4] Diels-Alder reaction and the hydrogenation reaction of the present invention are carried out in a pressure reactor, and the chlorination reaction and the Friedel-Crafts reaction are carried out under atmospheric pressure.

The reactants are analyzed with nuclear magnetic resonance (NMR) spectrum and a gas chromatography/mass selective detector (GC/MSD). A quantitative analysis using GC is performed under the following condition. The internal standard material is n-dodecane and the composition is determined in terms of the area ratio.

Capillary column—ULTRA 1 (Crosslinked methyl silicon gum)
50 m×0.22 m×0.33 μm
Carrier—nitrogen gas
Head pressure—18 psig
Oven—150 to 200° C., β=5° C./min; 200 to 280° C. (5° C./10 min), β=10° C./min
Detector and temperature—FID (280° C.)
Split ratio—50:1
Make up gas flow rate—38 ml/min

DETAILED DESCRIPTION OF THE INVENTION

Hereinafter, the present invention will be described in detail by way of the following examples, which are not intended to limit the scope of the present invention.

EXAMPLE 1

(i) 72 g (1 mol) of acrylic acid, 0.35 g of 4-t-butylcatechol and 288 g of benzene were added to a 1L-pressure reactor. After adding 70 g (1.3 mol) of 1,3-butadiene, the temperature was raised to 120° C. and, after 2 hours of reaction, the product was identified a 3-cyclohexene-1-carboxylic acid using $^1$H NMR spectrum and with a yield of more than 99% by gas chromatography.

$^1$H NMR (CDCl$_3$): δ1.70–1.82 (m, 1H), 1.94–2.35 (m, 5H), 2.49–2.75 (m, 1H), 5.59–5.79 (m, 2H)

3.2 g (2.5 wt. % of 3-cyclohexene-1-carboxylic acid) 3% Pd/C was added to the 3-cyclohexene-1-carboxylic acid solution and the reaction was activated at the temperature of 100° C. with a hydrogen pressure of 120 psi to yield cyclohexanecarboxylic acid with a conversion rate of more than 99%.

$^1$H NMR (CDCl$_3$): δ1.18–2.34 (m, 10OH), 2.35–2.40 (m, 1H)

(ii) 20.0 g (cyclohexanecarboxylic acid: 6.95 g, 0.054 mol) of the cyclohexanecarboxylic acid solution and 1.0 g of n-dodecane as an internal standard material were added to a reactor equipped with a condenser and a Dean-Stark water separator. After adding 90 ml of benzene, about 25 ml of benzene was distilled off in the nitrogen atmosphere to make the anhydrous solution. The temperature of the reactant solution was lowered to the atmospheric temperature and 6.0 ml (9.8 g, 0.082 mol) of thionyl chloride was added for one hour of reflux.

After the reaction, part of the reactant solution was collected and reacted with methanol including a small amount of triethylamine in order to identify the product, cyclohexanecarbonyl chloride. The yield of methyl cyclohexane carboxylate was analyzed by GC. As a result, cyclohexanecarbonyl chloride was produced with a conversion rate of more than 99% and a selectivity of more than 99%.

(iii) 10.86 g (0.081 mol) of anhydrous aluminum trichloride was added to the cyclohexanecarbonyl chloride solution, and the resulting solution was kept at an internal temperature of below 3° C. with a water/ice bath. After removal of the water/ice bath, the temperature was slowly raised to the reflux temperature and, after one hour, the product was identified as cyclohexyl phenyl ketone with a conversion rate of more than 99% and a selectivity of more than 99% with respect to cyclohexanecarbonyl chloride.

$^1$H NMR (CDCl$_3$): δ1.22–1.59 (m, 4H), 1.71–1.92 (m, 6H), 3.19–3.32 (m, 1H), 7.41–7.58 (m, 3H), 7.92–7.97 (m, 2H)

EXAMPLE 2

The procedures were performed in the same manner as described in the step (i) of Example 1, excepting that 3-cyclohexene-1-carboxylic acid was obtained with a yield of more than 99% without using any solvent including benzene.

The subsequent reactions, such as hydrogenation, chlorination and Friedel-Crafts reaction were carried out in the same manner as described in Example 1. The obtained product was identified as cyclohexyl, phenyl ketone with a conversion rate of more than 99% and a selectivity of more than 99% with respect to cyclohexanecarbonyl chloride.

EXAMPLE 3

The procedures were performed in the same manner as described in the step (ii) of Example 1, excepting that the ratio of thionyl chloride to cyclohexanecarboxylic acid was varied in the same reaction to prepare cyclohexanecarbonyl chloride. The results are presented in Table 1.

TABLE 1

Yield of cyclohexanecarbonyl chloride according to change of molar ratio of cyclohexanecarboxylic acid to thionyl chloride

| Cyclohexanecarboxylic acid:thionyl chloride (molar ratio) | Conversion rate | Selectivity |
| --- | --- | --- |
| 1.0:1.0 | 89 | >99 |
| 1.0:1.2 | 96 | >99 |
| 1.0:1.5 | >99 | >99 |
| 1.0:2.0 | >99 | >99 |

The subsequent Friedel-Crafts reaction was carried out in the same manner as described in Example 1. The obtained product was identified as cyclohexyl phenyl ketone with a conversion rate of more than 99% and a selectivity of more than 99% with respect to cyclohexanecarbonyl chloride.

EXAMPLE 4

The procedures were performed in the same manner as described in the step (ii) of Example 1, excepting that phosphorous trichloride was used instead of thionyl chloride as a chlorinating compound to prepare cyclohexanecarbonyl chloride.

More specifically, 20.0 g (cyclohexanecarboxylic acid: 6.95 g, 0.054 mol) of the cyclohexanecarboxylic acid solution and 1.0 g of n-dodecane as an internal standard material were added to a reactor equipped with a condenser and a Dean-Stark water separator. After adding 90 ml of benzene, about 25 ml of benzene was distilled off in the nitrogen atmosphere to make the internal solution anhydrous. The temperature of the reactant solution was lowered to the atmospheric temperature and 2.4 ml (3.77 g, 0.027 mol) of phosphorous trichloride was added for one hour of reflux.

After the reaction, part of the reactant solution was collected and reacted with methanol including a small amount of triethylamine in order to identify the product, cyclohexanecarbonyl chloride. The yield of methyl cyclohexane carboxylate was analyzed by GC. As a result, cyclohexanecarbonyl chloride was produced with a conversion rate of more than 99% and a selectivity of more than 99%.

The subsequent Friedel-Crafts reaction was carried out in the same manner as described in Example 1. The obtained product was identified as cyclohexyl phenyl ketone with a conversion rate of more than 99% and a selectivity of more than 99% with respect to cyclohexanecarbonyl chloride.

EXAMPLE 5

The procedures were performed in the same manner as described in the step (iii) of Example 1, excepting that the ratio of anhydrous aluminum trichloride to cyclohexanecarbonyl chloride was varied to prepare cyclohexyl phenyl ketone. The results are presented in Table 2.

TABLE 2

Yield of cyclohexyl phenyl ketone according to change of molar ratio of cyclohexanecarbonyl chloride to anhydrous aluminum trichloride

| Cyclohexanecarbonyl chloride:anhydrous aluminum trichloride (molar ratio) | Conversion rate | Selectivity |
| --- | --- | --- |
| 1.0:1.0 | 74 | >99 |
| 1.0:1.2 | 93 | >99 |
| 1.0:1.5 | >99 | >99 |
| 1.0:2.0 | >99 | >99 |

EXAMPLE 6

The procedures were performed in the same manner as described in Example 1, excepting that n-hexane was used as a solvent instead of benzene.

More specifically, (i) 72 g (1.0 mol) of acrylic acid, 0.35 g of 4-t-butylcatechol and 288 g of n-hexane were added to a 1 L-pressure reactor. After adding 70 g (1.3 mol) of 1,3-butadiene, the temperature was raised to 120° C. and, after 2 hours of reaction, the product was identified as 3-cyclohexene-1-carboxylic acid with a yield of more than 99% by using GC.

3.2 g (2.5 wt. % of 3-cyclohexene-1-carboxylic acid) 3% Pd/C was added to the 3-cyclohexene-1-carboxylic acid solution and the reaction was activated at the temperature of 100° C. with a hydrogen pressure of 120 psi to yield cyclohexanecarboxylic acid with a conversion rate of more than 99%.

(ii) 25 ml (cyclohexanecarboxylic acid: 6.0 g, 0.047 mol) of the cyclohexanecarboxylic acid solution and 1.0 g of n-dodecane as an internal standard material were added to a reactor equipped with a condenser and a Dean-Stark water separator. After adding 30 ml of benzene and 60 ml of n-hexane, about 25 ml of n-hexane was distilled off in the nitrogen atmosphere to make the internal solution anhydrous. The temperature of the reactant solution was lowered to the atmospheric temperature and 3.4 ml (5.55 g, 0.047 mol) of thionyl chloride was added for one hour of reflux. After the reaction, part of the reactant solution was collected and reacted with methanol in order to identify the product, cyclohexanecarbonyl chloride, the selectivity of which was determined as 99%.

(iii) 9.36 g (0.070 mol) of anhydrous aluminum trichloride was added to the cyclohexanecarbonyl chloride solution in a water/ice bath with stirring for 20 minutes. After removal of the water/ice bath, the temperature was slowly raised to the reflux temperature and, after one hour, the product was identified as cyclohexyl phenyl ketone with a conversion rate of more than 99% and a selectivity of more than 99% with respect to cyclohexanecarbonyl chloride.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

As described above, the present invention involves (a) a [2+4] Diels-Alder reaction of a 1,3-butadiene and an acrylic acid in the presence or absence of benzene or a non-aromatic organic solvent to prepare a 3-cyclohexene-1-carboxylic acid; (b) a hydrogenation reaction of the 3-cyclohexene-1-carboxylic acid into a cyclohexanecarboxylic acid; (c) a chlorination reaction in the solution of the cyclohexanecarboxylic acid without separation or purification of the cyclohexanecarboxylic acid to prepare a cyclohexanecarbonyl chloride; and (d) a Friedel-Crafts reaction in the same reactor without a step of separating or purifying the cyclohexanecarboxylic acid, thereby preparing a cyclohexyl phenyl ketone industrially useful with a high selectivity and a high yield.

What is claimed is:

1. A method for preparing a cyclohexyl phenyl ketone from a 1,3-butadiene and an acrylic acid, the method comprising:

(a) carrying out a [2+4] Diels-Alder reaction of the 1,3-butadiene and the acrylic acid in the presence or absence of a solvent to prepare a 3-cyclohexene-1-carboxylic acid;

(b) carrying out a hydrogenation reaction of the 3-cyclohexene-1-carboxylic acid to prepare a cyclohexanecarboxylic acid;

(c) carrying out a chlorination reaction in the solution of the cyclohexanecarboxylic acid without separation or purification of the cyclohexanecarboxylic acid to prepare a cyclohexanecarbonyl chloride; and (d) continuously carrying out a Friedel-Crafts reaction of the cyclohexanecarbonyl chloride in the same reactor without separation or purification of an intermediate to prepare a cyclohexyl phenyl ketone.

2. The method as claimed in claim 1, the solvent includes benzene or a non-aromatic organic solvent.

3. The method as claimed in claim 2, the non-aromatic organic solvent includes cyclohexane, hexane, heptane, octane, tetrahydrofuran, dioxane, ether, and a mixture thereof.

4. The method as claimed in claim 1, the [2+4] Diels-Alder reaction is carried out in the presence of a polymerization inhibitor in the temperature range of 80 to 200° C.

5. The method as claimed in claim 1, the hydrogenation reaction being carried out in the temperature range of 80 to 120° C. with a hydrogen pressure of 80 to 120 psi.

6. The method as claimed in claim 1, the chlorination reaction is carried out using thionyl chloride or phosphorous trichloride.

7. The method as claimed in claim 1, the chlorination reaction is carried out using thionyl chloride or phosphorous trichloride at an equivalence ratio of 1 to 2 with respect to the cyclohexane carboxylic acid.

8. The method as claimed in claim 6, the chlorination reaction is carried out using thionyl chloride or phosphorous trichloride at an equivalence ratio of 1 to 2 with respect to the cyclohexane carboxylic acid.

9. The method as claimed in claim 1, the Friedel-Crafts reaction is carried out in the presence of an anhydrous aluminum trichloride catalyst.

10. The method as claimed in claim 1, the Friedel-Crafts reaction is carried out in the presence of an anhydrous aluminum trichloride at an equivalence ratio of 1 to 3 with respect to the cyclohexane carbonyl chloride.

11. The method as claimed in claim 9, the Friedel-Crafts reaction is carried out in the presence of an anhydrous aluminum trichloride at an equivalence ratio of 1 to 3 with respect to the cyclohexane carbonyl chloride.

* * * * *